United States Patent
Sinha et al.

(10) Patent No.: US 10,980,447 B2
(45) Date of Patent: Apr. 20, 2021

(54) SYSTEM AND METHOD FOR TRACKING BODY JOINTS

(71) Applicant: Tata Consultancy Services Limited, Mumbai (IN)

(72) Inventors: Sanjana Sinha, Kolkata (IN); Brojeshwar Bhowmick, Kolkata (IN); Aniruddha Sinha, Kolkata (IN); Abhijit Das, Bengal (IN)

(73) Assignee: Tata Consultancy Limited Services, Mumbai (IN)

( * ) Notice: Subject to any disclaimer, the term of this patent is extended or adjusted under 35 U.S.C. 154(b) by 406 days.

(21) Appl. No.: 15/908,731

(22) Filed: Feb. 28, 2018

(65) Prior Publication Data

US 2019/0008421 A1    Jan. 10, 2019

(30) Foreign Application Priority Data

Jul. 7, 2017    (IN) .............................. 201721024066

(51) Int. Cl.
*A61B 5/11*        (2006.01)
*G06T 7/246*        (2017.01)
(Continued)

(52) U.S. Cl.
CPC ........ *A61B 5/1128* (2013.01); *G06K 9/00335* (2013.01); *G06T 7/251* (2017.01);
(Continued)

(58) Field of Classification Search
CPC ... A61B 5/1128; A61B 5/1124; A61B 5/1121; A61B 5/1122; G06T 7/277; G06T 7/251;
(Continued)

(56) References Cited

U.S. PATENT DOCUMENTS

| 2010/0197395 A1* | 8/2010 | Geiss ..................... A63F 13/04 463/31 |
| 2014/0219550 A1* | 8/2014 | Popa .................. G06K 9/00342 382/154 |

(Continued)

OTHER PUBLICATIONS

Raskin et al., "Dimensionality reduction using a Gaussian Process Annealed Particle Filter for tracking and classification of articulated body motions", Apr. 2011, Elsevier, Computer Vision and Image Understanding, vol. 115, is. 4, p. 503-519. (Year: 2011).*

(Continued)

*Primary Examiner* — Vincent Rudolph
*Assistant Examiner* — Timothy Choi
(74) *Attorney, Agent, or Firm* — Finnegan, Henderson, Farabow, Garrett & Dunner LLP (57) ABSTRACT

Body joint tracking is applied in various industries and medical field. In body joint tracking, marker less devices plays an important role. However, the marker less devices are facing some challenges in providing optimal tracking due to occlusion, ambiguity, lighting conditions, dynamic objects etc. System and method of the present disclosure provides an optimized body joint tracking. Here, motion data pertaining to a first set of motion frames from a motion sensor are received. Further, the motion data are processed to obtain a plurality of 3 dimensional cylindrical models. Here, every cylindrical model among the plurality of 3 dimensional cylindrical model represents a body segment. The coefficients associated with the plurality of 3 dimensional cylindrical models are initialized to obtain a set of initialized cylindrical models. A set of dynamic coefficients associated with the initialized cylindrical models are utilized to track joint motion trajectories of a set of subsequent frames.

5 Claims, 6 Drawing Sheets

300

(51) Int. Cl.
    G06T 7/277       (2017.01)
    G06K 9/00        (2006.01)
(52) U.S. Cl.
    CPC .... *G06T 7/277* (2017.01); *G06T 2207/10028* (2013.01); *G06T 2207/30008* (2013.01); *G06T 2207/30196* (2013.01); *G06T 2207/30241* (2013.01)
(58) Field of Classification Search
    CPC ...... G06T 2207/10028; G06K 9/00335; G06K 9/00342; G06K 9/00348; G06K 9/00355; G06K 9/00362; G06K 9/00369; G06K 9/00375; G06K 9/00382; G06K 9/000389; G06K 2009/00395
    See application file for complete search history.

(56) References Cited

U.S. PATENT DOCUMENTS

2018/0211104 A1\* 7/2018 Zhao .................. G06K 9/00355
2020/0074161 A1\* 3/2020 Murakami ................ G06T 7/20

OTHER PUBLICATIONS

Haggag et al., "Efficacy Comparison of Clustering Systems for Limb Detection", Jun. 2014, IEEE, 9th Int. Conf. on System of Systems Engineering, p. 148-153. (Year: 2014).*

Devanne et al., "3-D Human Action Recognition by Shape Analysis of Motion Trajectories on Riemannian Manifold", Jul. 2015, IEEE, Transactions on Cybernetics, vol. 45, No. 7, p. 1340-1352. (Year: 2015).*

Mure-Duboise et al., "Fusion of Time of Flight Camera Point Clouds", Oct. 2008, HAL, Workshop on Multi-camera and Multi-modal Sensor Fusion ALgorithms and Applications—M2SFA2 2008, p. 1-12 (Year: 2008).*

Munaro et al., "3D Reconstruction of Freely Moving Persons for Re-Identification with a Depth Sensor", Jun. 2014, IEEE, 2014 IEEE Int. Conf. on Robotics and Automation, p. 4512-4519. (Year: 2014).*

Lehment et al., "Automated Pose Estimation in 3D Point Clouds Applying Annealing Particle Filters and Inverse Kinematics on a GPU", Jun. 18, 2010, IEEE, 2010 IEEE Computer Society Conference on Computer Vision and Pattern Recognition—Workshops, p. 87-92. (Year: 2010).*

Choi et al., "RGB-D Object Tracking: A Particle Filter Approach on GPU", Nov. 7, 2013, IEEE, 2013 IEEE/RSJ International Conference on Intelligent Robots and Systems (IROS), p. 1084-1091. (Year: 2013).*

Pons-Moll et al., "Outdoor Human Motion Capture using Inverse Kinematics and von Mises-Fisher Sampling", Nov. 13, 2011, IEEE, 2011 International Conference on Computer Vision, p. 1243-1250. (Year: 2011).*

Boesen, A. et al., "Unscented Kalman Filtering for Articulated Human Tracking", Scandinavian Conference on Image Analysis, Springer, Berlin, Heidelberg, 2011, 10 pages.

Valgma, L., "3D reconstruction using Kinect v2 camera", Tartu, 2016, 42 pages Retrieved from https://www.tuit.ut.ee/sites/default/files/tuit/atprog-courses-bakalaureuset55-loti.05.029-lembit-valgma-text-20160520.pdf.

\* cited by examiner

SYSTEM AND METHOD FOR TRACKING BODY JOINTS

PRIORITY CLAIM

This U.S. patent application claims priority under 35 U.S.C. § 119 to: India Application No. 201721024066, filed on Jul. 7, 2017. The entire contents of the aforementioned application are incorporated herein by reference.

TECHNICAL FIELD

The embodiments herein generally relates, in general, to motion tracking and, in particular, to a system and method for tracking body joints.

BACKGROUND

Tracking body joints is key research field and applied in a variety of applications including computer animation, video games, medical therapy, surveillance, human machine interaction and athlete performance analysis. Moreover, the joint motion analysis is an important aspect in health monitoring of patients suffering from neurological disorders, post-stroke patients, and an elderly subjects. In real-time body joint tracking, accuracy in tracking is a challenging task. The challenge is due to change in appearance due to non-rigid motion of a subject undergoing test, clothing, view point and lighting.

Conventional real-time body joint tracking methods are marker-based and requires a subject undergoing test to wear obtrusive devices. Moreover, the conventional marker based joint tracking methods are complex, difficult to maintain, extremely expensive and may not be viable for a prolonged rehabilitation therapy. Hence marker less joint tracking systems are used for tracking body joints in real-time. However, the conventional marker less real-time body joint tracking systems are facing challenges to obtain optimized body joint tracking due to occlusion, ambiguity, lighting conditions and dynamic objects and the like.

SUMMARY

Embodiments of the present disclosure present technological improvements as solutions to one or more of the above-mentioned technical problems recognized by the inventors in conventional systems. For example, in one embodiment, a method for tracking body joints is provided. The method includes receiving, motion data pertaining to a first set of motion frames from a motion sensor device, wherein the motion data comprises an initial joint motion data and a plurality of depth frames, wherein the initial joint motion data comprises locations in 3 dimensional world coordinates of a plurality of body joints associated with the plurality of depth frames and each depth frame among the plurality of depth frames comprises a set of 2 dimensional image coordinates and a depth value, by one or more hardware processors. Further, the method includes, initializing, a plurality of cylindrical models for each motion frame among the first set of motion frames by processing the initial joint motion data and the plurality of depth frames, wherein the plurality of cylindrical models represents a plurality of body segments, connecting adjacent body joints among the plurality of body joints, by the one or more hardware processors. Furthermore, the method includes tracking, by the one or more hardware processors, the plurality of initialized cylindrical models to obtain one or more optimized motion trajectories of the plurality of body joints in a plurality of motion frames received in succession to the first set of motion frames based on one or more direction angles and one or more base coordinates associated with each of the plurality of cylindrical models, wherein the tracking is performed by utilizing particle filter mechanism, by the one or more hardware processors.

In another aspect, a system for tracking body joints is provided. The system includes one or more memories comprising programmed instructions and repository for storing the one or more motion data, a database; and one or more hardware processors operatively coupled to the one or more memories, wherein the one or more hardware processors are capable of executing the programmed instructions stored in the one or more memories, a motion sensor device and a joint tracking unit, wherein the joint tracking unit is configured to receive, motion data pertaining to a first set of motion frames from a motion sensor device, wherein the motion data comprises an initial joint motion data and a plurality of depth frames, wherein the initial joint motion data comprises locations in 3 dimensional world coordinates of a plurality of body joints associated with the plurality of depth frames and each depth frame among the plurality of depth frames comprises a set of 2 dimensional image coordinates and a depth value. Further, the joint tracking unit is configured to initialize, a plurality of cylindrical models for each motion frame among the first set of motion frames by processing the initial joint motion data and the plurality of depth frames, wherein the plurality of cylindrical models represents a plurality of body segments, connecting adjacent body joints among the plurality of body joints. Furthermore, the joint tracking unit is configured to track, the plurality of initialized cylindrical models to obtain one or more optimized motion trajectories of the plurality of body joints in a plurality of motion frames received in succession to the first set of motion frames based on one or more direction angles and one or more base coordinates associated with each of the plurality of cylindrical models, wherein the tracking is performed by utilizing particle filter mechanism.

In yet another aspect, a computer program product comprising a non-transitory computer-readable medium having embodied therein a computer program for system and method for tracking body joints, is provided. The computer readable program, when executed on a computing device, causes the computing device to receive, motion data pertaining to a first set of motion frames from a motion sensor device, wherein the motion data comprises an initial joint motion data and a plurality of depth frames, wherein the initial joint motion data comprises locations in 3 dimensional world coordinates of a plurality of body joints associated with the plurality of depth frames and each depth frame among the plurality of depth frames comprises a set of 2 dimensional image coordinates and a depth value. Further computer readable program, when executed on a computing device, causes the computing device to initialize, a plurality of cylindrical models for each motion frame among the first set of motion frames by processing the initial joint motion data and the plurality of depth frames, wherein the plurality of cylindrical models represents a plurality of body segments, connecting adjacent body joints among the plurality of body joints. Furthermore computer readable program, when executed on a computing device, causes the computing device to track, the plurality of initialized cylindrical models to obtain one or more optimized motion trajectories of the plurality of body joints in a plurality of motion frames received in succession to the first set of motion frames based on one or more direction angles and one or more base coordinates associated with each of the plurality of cylindrical models, wherein the tracking is performed by utilizing particle filter mechanism.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

In the field of motion tracking, tracking body joints plays a vital role. Since the conventional methods are performing tracking of body joints by utilizing marker based methods and the marker based methods needs some obtrusive devices to be worn by the subjects undergoing tests, marker less body joints tracking methods are prominent. The marker less motion body joint tracking methods includes a motion sensor to capture a plurality of motion data. For example, Kinect® V1 is marker less motion sensing device mainly used for tracking body joints. However, the motion sensor based body joint tracking methods are prone to occlusion, IR interference, lighting conditions and distance from the motion sensor.

The present subject matter overcomes the limitations of the conventional joint tracking methods by modeling a set of 3 dimensional point clouds associated with a body (for example, human body and animal body). Here, a set of 3 dimensional cylindrical models are initialized by utilizing the set of 3 dimensional point cloud data. Further, the set of initialized 3 dimensional cylindrical models are tracked based on a set of dynamic parameters associated with the set of initialized cylindrical models to obtain an optimized joint motion trajectories associated with the body. Here, the optimized joint locations are derived directly in 3 dimensional coordinate space to reduce adverse effects of noise associated with a depth data from depth sensor of a motion sensor device. An implementation of the system and method for tracking body joints is described further in detail with reference to FIGS. 1 through 5C.

Referring now to the drawings, and more particularly to FIGS. 1 through 5C, where similar reference characters denote corresponding features consistently throughout the figures, there are shown preferred embodiments and these embodiments are described in the context of the following exemplary system and/or method.

Figure 1:
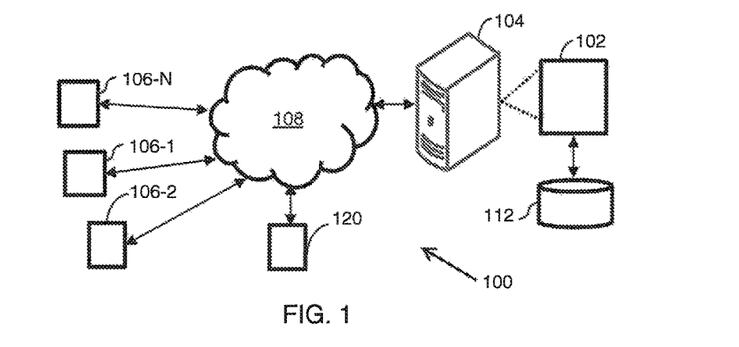
FIG. 1 illustrates a network environment implementing a system and method for tracking body joints, according to some embodiments of the present disclosure.

FIG. 1 illustrates a network environment 100 implementing a system 102 for tracking body joints, according to an example embodiment of the present subject matter. The system for tracking body joints 102, hereinafter referred to as the system 102, is configured for tracking body joints using motion data received from a motion sensor device 120. In an embodiment, motion sensor device 120 can be a Kinect® V1 device for monitoring subject's movements. The system 102 may be embodied in a computing device, for instance a computing device 104.

Although the present disclosure is explained considering that the system 102 is implemented on a server, it may be understood that the system 102 may also be implemented in a variety of computing systems, such as a laptop computer, a desktop computer, a notebook, a workstation, a cloud-based computing environment and the like. In one implementation, the system 102 may be implemented in a cloud-based environment. It will be understood that the system 102 may be accessed by multiple users through one or more user devices 106-1, 106-2 . . . 106-N, collectively referred to as user devices 106 hereinafter, or applications residing on the user devices 106. Examples of the user devices 106 may include, but are not limited to, a portable computer, a personal digital assistant, a handheld device, a Smartphone, a Tablet Computer, a workstation and the like. The user devices 106 are communicatively coupled to the system 102 through a network 108.

In an embodiment, the network 108 may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 108 may include a variety of network devices, including routers, bridges, servers, computing devices, storage devices. The network devices within the network 108 may interact with the system 102 through communication links.

As discussed above, the system 102 may be implemented in a computing device 104, such as a hand-held device, a laptop or other portable computer, a tablet computer, a mobile phone, a PDA, a smartphone, and a desktop computer. The system 102 may also be implemented in a workstation, a mainframe computer, a server, and a network server. In an embodiment, the system 102 may be coupled to a data repository, for example, a repository 112. The repository 112 may store data processed, received, and generated by the system 102. In an alternate embodiment, the system 102 may include the data repository 112. The components and functionalities of the system 102 are described further in detail with reference to FIG. 2.

Figure 2:
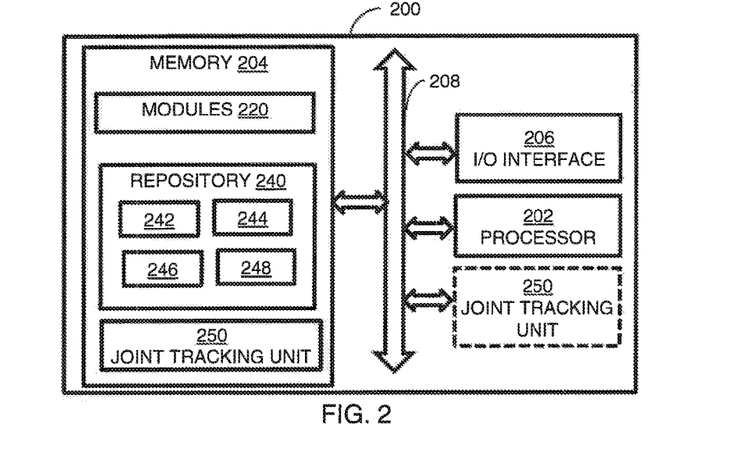
FIG. 2 illustrates a block diagram of a system and method for tracking body joints, according to some embodiments of the present disclosure.

FIG. 2 illustrates a block diagram of a body joint tracking system 200 for tracking body joints, according to some embodiments of the present disclosure. The body joint tracking system 200 (hereinafter referred to as system 200) may be an example of the system 102 (FIG. 1). In an example embodiment, the system 200 may be embodied in, or is in direct communication with the system, for example the system 102 (FIG. 1). The system 200 includes or is otherwise in communication with one or more hardware processors such as a processor 202, at least one memory such as a memory 204, an I/O interface 206 and a joint tracking unit 250. In an embodiment, the joint tracking unit 250 can be implemented as a standalone unit in the system 200 comprising an point cloud segmentation module (not shown in FIG. 2), a cylinder model fitting module (not shown in FIG. 2), a state propagation module (not shown in FIG. 2) and a likelihood estimation module (not shown in FIG. 2). In another embodiment, the joint tracking unit 250 can be implemented as a module in the memory 204 comprising the point cloud segmentation module (not shown in FIG. 2), the cylinder model fitting module (not shown in FIG. 2), the state propagation module (not shown in FIG. 2) and the likelihood estimation module (not shown in FIG. 2). The processor 202, memory 204, and the I/O interface 206 may be coupled by a system bus such as a system bus 208 or a similar mechanism.

The I/O interface 206 may include a variety of software and hardware interfaces, for example, a web interface, a graphical user interface, and the like. The interfaces 206 may include a variety of software and hardware interfaces, for example, interfaces for peripheral device(s), such as a keyboard, a mouse, an external memory, a camera device, and a printer. Further, the interfaces 206 may enable the system 102 to communicate with other devices, such as web servers and external databases. The interfaces 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 206 may include one or more ports for connecting a number of computing systems with one another or to another server computer. The I/O interface 206 may include one or more ports for connecting a number of devices to one another or to another server.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220 and the joint tracking unit 250. The modules 220 may include routines, programs, objects, components, data structures, and so on, which perform particular tasks or implement particular abstract data types.

The memory 204 also includes module(s) 220 and a data repository 240. The module(s) 220 include programs or coded instructions that supplement applications or functions performed by the body joint tracking system 200. The modules 220, amongst other things, can include routines, programs, objects, components, and data structures, which perform particular tasks or implement particular abstract data types. The modules 220 may also be used as, signal processor(s), state machine(s), logic circuitries, and/or any other device or component that manipulates signals based on operational instructions. Further, the modules 220 can be used by hardware, by computer-readable instructions executed by a processing unit, or by a combination thereof. The modules 220 can include various sub-modules (not shown). The module 220 may include computer-readable instructions that supplement applications or functions performed by the signal analysis system 200.

The data repository 240 may include received motion tracking data 242, 3D world coordinate data 244, a plurality of body joints 246 and other data 248. Further, the other data 248 amongst other things, may serve as a repository for storing data that is processed, received, or generated as a result of the execution of one or more modules in the module(s) 220 and the modules associated with the joint tracking unit 250.

Although the data repository 240 is shown internal to the body joint tracking system 200, it will be noted that, in alternate embodiments, the data repository 240 can also be implemented external to the body joint tracking system 200, where the data repository 240 may be stored within a database (not shown in FIG. 2) communicatively coupled to the body joint tracking system 200. The data contained within such external database may be periodically updated. For example, new data may be added into the database (not shown in FIG. 2) and/or existing data may be modified and/or non-useful data may be deleted from the database (not shown in FIG. 2). In one example, the data may be stored in an external system, such as a Lightweight Directory Access Protocol (LDAP) directory and a Relational Database Management System (RDBMS). In another embodiment, the data stored in the data repository 240 may be distributed between the body joint tracking system 200 and the external database.

The joint tracking unit 250 of the body joint tracking system 200 can be configured to receive, a plurality of motion data pertaining to a first set of motion frames from the motion sensor device 120. The motion data comprises an initial joint motion data and a plurality of depth frames, wherein the initial joint motion data comprises locations in 3 dimensional world coordinates represented as $\vec{C}_t^j=[X, Y, Z]^T$ of a plurality of body joints associated with the plurality of depth frames and each depth frame among the plurality of depth frames comprises a set of 2D image coordinates and a depth value. The depth value can be a distance in millimeter between the subject undergoing exercise and the motion sensor device 120. A line joining two adjacent body joints i and j can be $\vec{b}_t^{(i,j)}$. The line $\vec{b}_t^{(i,j)}$ can be represented as a body segment $B^{(i,j)}$ connecting two adjacent body joints i and j. Further, the line $\vec{b}_t^{(i,j)}$ is associated with a direction information. In an embodiment, the Kinect® V1 device is utilized for capturing the plurality of motion data including the initial joint motion data and the plurality of depth frames at 30 fps, at a distance of 1.8 m to 2.5 m from the subject undergoing exercise.

In an embodiment, a plurality of active joint Range Of Motion (ROM) data pertaining to upper body portion (for example, shoulder abduction, shoulder flexion and extension, Elbow flexion and extension) of the subject undergoing exercise is received from the motion sensor device 120. In the context of present disclosure, ROM refers to any kind of movement of a body during dynamic postures involving joints in the body such as ROM exercises.

Further, the joint tracking unit 250 of the body joint tracking system 200 can be further configured to initialize a plurality of cylindrical models for each motion frame among the first set of motion frames by processing the initial joint motion data and the plurality of depth frames. Here, the plurality of cylindrical models represents a plurality of body segments, connecting adjacent body joints among the plurality of body joints. Here, a plurality of 3 dimensional point clouds corresponding to the plurality of depth frames are obtained by mapping every 2D pixel coordinates (x, y) to the 3 dimensional world coordinates (X,Y,Z) based on a perspective projection as given below:

$$X = \frac{(x-c_x)}{f_x}d,$$

$$Y = \frac{(y-c_y)}{f_y}d,$$

Z=d, where $f_x$ and $f_y$ refers to focal lengths of a depth sensor associated with the motion sensor device 120 along x axis and y axis respectively, d is the depth value and $(c_x,c_y)$ are a coordinates of an image center. Further, the plurality of 3 dimensional point clouds $P_t$ are segmented based on a segmentation threshold to obtain a first set of segmented 3 dimensional point clouds $S_t$ representing a body segment $B^{(i,j)}$ using the equation, $$S_t=\{\vec{P}\in P_t:\|(\vec{P}-\vec{b}_t^{(i,j)})\|<r\} \quad\rightarrow(1)$$

Here, r is the segmentation threshold obtained based on an Euclidean distance computed for 3 dimensional world coordinates corresponding to the plurality of body joints of the initial joint motion data. Here, the first set of segmented 3 dimensional point clouds $S_t$ corresponds to the plurality of body segments $B^{(i,j)}$ for every joint pair (i, j). Further, the first set of segmented 3 dimensional point clouds $S_t$ corresponding to the plurality of body segments $B^{(i,j)}$ are smoothened and reconstructed prior to model fitting to reduce the model outliers. The smoothened first set of segmented 3 dimensional point clouds $S'_t$ are reconstructed and smoothened by applying at least one surface reconstruction mechanism. In an embodiment, Moving Least Squares (MLS) can be utilized for the surface reconstruction and smoothening. The surface reconstruction and smoothening on the first set of segmented 3 dimensional point clouds $S_t$ provides a new set of segmented point cloud $S'_t$ corresponding to the plurality of body segments $B^{(i,j)}$. Further, the plurality of cylindrical models are fitted to the new set of segmented point cloud $S'_t$ corresponding to the plurality of body segments $B^{(i,j)}$. In an embodiment, $M_t$ denotes a best fitting cylindrical model at time t with maximum inlier count. Each cylindrical model among the plurality of cylindrical models includes a set of cylinder coefficients represented by $M^{(i,j)}=\{\vec{b}, \vec{d}, R, L\}$, where, R denotes radius, L denotes length, $\vec{d}$ denotes direction angles and $\vec{b}$ denotes base coordinates. The set of cylindrical coefficients $M^{(i,j)}$ are obtained from the plurality of cylindrical models $M_t$ at different time instances t=1, 2, 3 ... n, associated with each motion frame among the first set of motion frames. The radius R of the plurality of cylindrical models can be initialized to a mean radius value obtained from the cylinder radius in $M_t$ corresponding to the plurality of motion frames. The direction angles $\vec{d}$ of the plurality of cylindrical models is initialized to a mean direction value $\vec{d}=[d_x, d_y, d_z]^T$ obtained from the cylinder directions in $M_t$ corresponding to from the plurality of motion frames. The base $\vec{b}$ of the plurality of cylindrical models can be initiated to an average base value $\vec{b}=[b_x, b_y, b_z]^T$, obtained by projecting a plurality of joint center coordinates $\vec{C}_t^i$ in the initial joint motion data to an axis of a corresponding cylindrical model $M_t$ from the plurality of motion frames. The length L of the plurality of cylindrical models can be initialized to a mean length value represented as $\|\vec{b}_t^{(i,j)}\|$(t=1, 2 ... n), obtained from a distance between adjacent body joints in the initial joint motion data for plurality of motion frames.

Further the joint tracking unit 250 of the body joint tracking system 200 can be configured to track the plurality of initialized cylindrical models to recover motion trajectories $Tr_j=\{(\vec{C}_t^j, t)|t=1, 2 ... T\}$ of the plurality of body joints in a plurality of motion frames received in succession to the first set of motion frames based on direction angles $\vec{d}$ and base $\vec{b}$ coordinates associated with each of the plurality of cylindrical models. Here, the tracking is performed by utilizing a particle filter mechanism. The method of tracking by utilizing the particle filter mechanism is explained as follows: Here, a plurality of initialized cylindrical models and a second set of segmented point cloud data are received. The second set of segmented point cloud data corresponds to the plurality of motion frames received in succession to the first set of motion frames from the motion sensor device 120. The plurality of initialized cylindrical models are represented as a plurality of particles $p^{(k)}$ where k=1, 2 ... N. The particle filter mechanism approximates a state conditional density of the initialized cylindrical model $M^{(i,j)}$ by utilizing a set of N particles $p^{(k)}$, where k=1, 2 ... N. Every particle $p^{(k)}$ is associated with a state $X^{(k)}$ and a weight $\pi^{(k)}$. The state and the weight values can be updated iteratively. The state $X^{(k)}$ of a particle is represented by the direction angles $\vec{d}$ and base $\vec{b}$ coordinates, and a weight. At every time instance t, the plurality of particles $p^{(k)}$ propagates to a new state. The propagation is determined by a state space model based on a state propagation rule. The state propagation rule is obtained from the plurality of initialized cylindrical models. For example, At time instance t, the particle $p^{(k)}$, has a state $X_t^{(k)} = [\vec{b}_t, \vec{\theta}_t]^T$ where $\vec{b}_t = [b_x, b_y, b_z]^T$ represents the cylinder base coordinates and $\vec{\theta}_t = [\theta_x, \theta_y, \theta_z]^T$ represents the direction angles with x, y and z axes. The direction of the cylindrical model represented by particle $p^{(k)}$ among the plurality of cylindrical models can be obtained as $\vec{d}_t = [d_x, d_y, d_z]^T = [\cos\theta_x, \cos\theta_y, \cos\theta_z]^T$. The state $X_t^{(k)}$ of the particle $p^{(k)}$, at a time instance t is updated according to the state propagation rule referred to as equation 2 and equation 3.

$$\vec{\theta}_t = \vec{\theta}_{t-1} + (\vec{\theta}_{t-1} - \vec{\theta}_{t-2}) + N(0, \sigma_\theta^2) \quad \rightarrow (2)$$

$$\vec{b}_t = \vec{b}_{t-1} + N(0, \sigma_b^2) \quad \rightarrow (3)$$

Where, $\sigma_\theta^2$ and $\sigma_b^2$ are variance of Gaussian noise with zero mean for $\vec{\theta}$ and $\vec{b}$ respectively. The weight $\pi^{(k)}$ of a particle $P^{(k)}$ among the plurality of particles represents a likelihood of observing the new segmented point cloud $S'_t$ for a propagated state. The updating of weight $\pi^{(k)}$ is performed by an observation model based on a weight update rule. The weight update rule is obtained from the second set of segmented point cloud data and the plurality of initialized cylindrical models. For example, the weight $\pi^{(k)}$ of the particle $P^{(k)}$ can be updated by utilizing the weight update rule referred to as equation 4.

$$\pi_t^{(k)} = e^{-\frac{D^2}{2\sigma^2}} \quad (4)$$

Where $\sigma^2$ is variance of Gaussian likelihood function. D is the sum of all distances d of the cloud points $\vec{P} \in S'_t$ from the cylindrical model represented by a particle $p^{(k)}$. The distance d can be calculated by utilizing equation 5.

$$d = \alpha d_n + (1-\alpha)(d_e - R) \quad \rightarrow (5)$$

Where, $0 < \alpha < 1$ and $d_n$, represents an angular distance between a surface normal $\hat{n}_p$ of the point cloud $\vec{P}$ and a unit vector $\hat{n}$, normal to a cylindrical surface of the cylindrical model and $d_e$ is the Euclidean distance between $\vec{P}$ and the axis of the cylindrical model $\vec{d}_t$. If the distance of new segmented point clouds $S'_t$ from the axis of the cylindrical model $\vec{d}_t$ of the particle $P^{(k)}$ is lower the probability of correctness of state prediction of the particle is greater. Further, the cylindrical coefficients of the optimal cylindrical model $M'^{(i,j)}$ are obtained from a weighted average of the set of cylindrical coefficients—of N number of particles $P^{(k)}$. Further, the optimized temporal trajectories $Tr_i$ and $Tr_j$ corresponding to the joints i and j of the optimal cylindrical model are recovered from a set of end points of the optimal cylindrical model $M'^{(i,j)}$.

Figure 3:
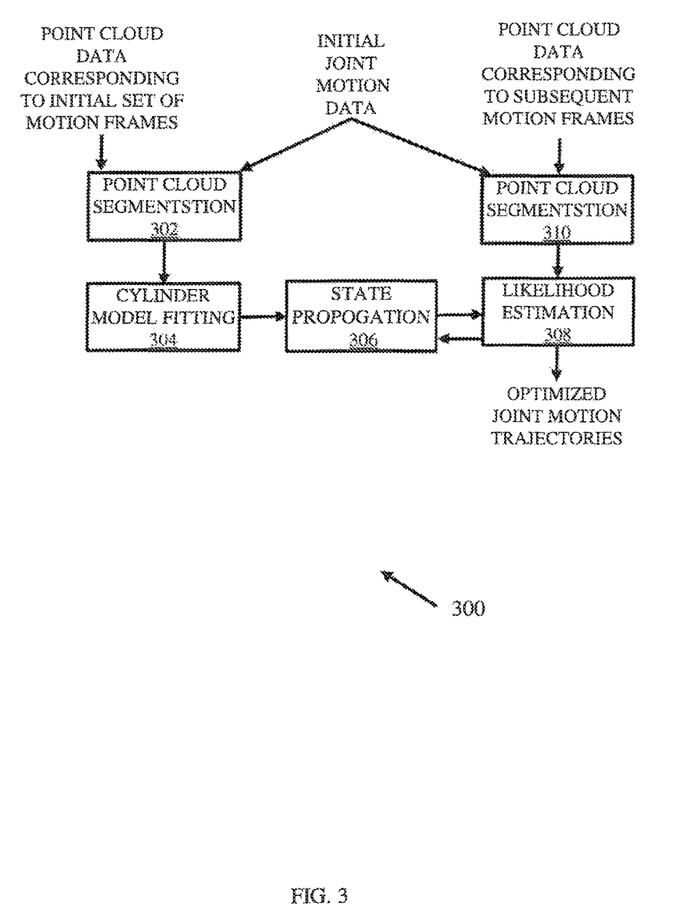
FIG. 3 depicts an architecture diagram for a system and method for tracking body joints according to some embodiments of the present disclosure.

FIG. 3 depicts an architecture diagram 300 for a system and method for body joint tracking according to some embodiments of the present disclosure. Here, the first set of point cloud data corresponding to the initial set of motion frames and the initial joint motion data are given to the point cloud segmentation module 302. The point cloud segmentation module 302 segments the point cloud data corresponding to the initial set of motion frames into a first set of segmented point clouds. Here the first set of segmented point clouds represents the plurality of body segments. The segmentation is performed by utilizing the initial joint motion data. Further, the plurality of cylindrical models are fitted into the first set of segmented point clouds by the cylinder model fitting module 304. Here, the set of coefficients associated with the plurality of cylindrical models are initialized to obtain the plurality of initialized cylindrical models. Every cylinder among the plurality of initialized cylindrical models represents the corresponding body segment. Here the body segment is connecting two adjacent body joints. Further, a second set of segmented point cloud data corresponding to the plurality of motion frames received in succession to the first set of motion frames from the motion sensor device is received. The second set of point cloud data is segmented using the initial joint motion data by the point cloud segmentation module 310. Further, every body segment corresponding to the plurality of initialized cylindrical models are represented as the particle. Every particle is associated with the corresponding state and the corresponding weight. The state includes base of the initialized cylindrical model and the direction angles of the initialized cylindrical model. The states are propagated based on the state propagation rule by the state propagation module 306. The state propagation module 306 utilizes the state space model and the state propagation rule is based on the plurality of initialized cylindrical models. The weight associated with the particle is updated by the likelihood estimation module 308 based on the weight update rule. The weight update rule is based on the second set of segmented point cloud data and the initialized cylindrical model. The likelihood estimation module 308 utilizes the observation module. Further, a cylindrical model among the plurality of initialized cylindrical model having maximum weight is selected as an optimal cylindrical model. Here, the cylindrical coefficients of the optimal cylindrical model are obtained from a weighted average of the set of cylindrical coefficients of N number of particles associated with the plurality of initialized cylindrical models. Further, the optimized temporal trajectories $Tr_i$ and $Tr_j$ corresponding to the joints i and j of the optimal cylindrical model are recovered from a set of end points of the optimal cylindrical model.

Figure 4:
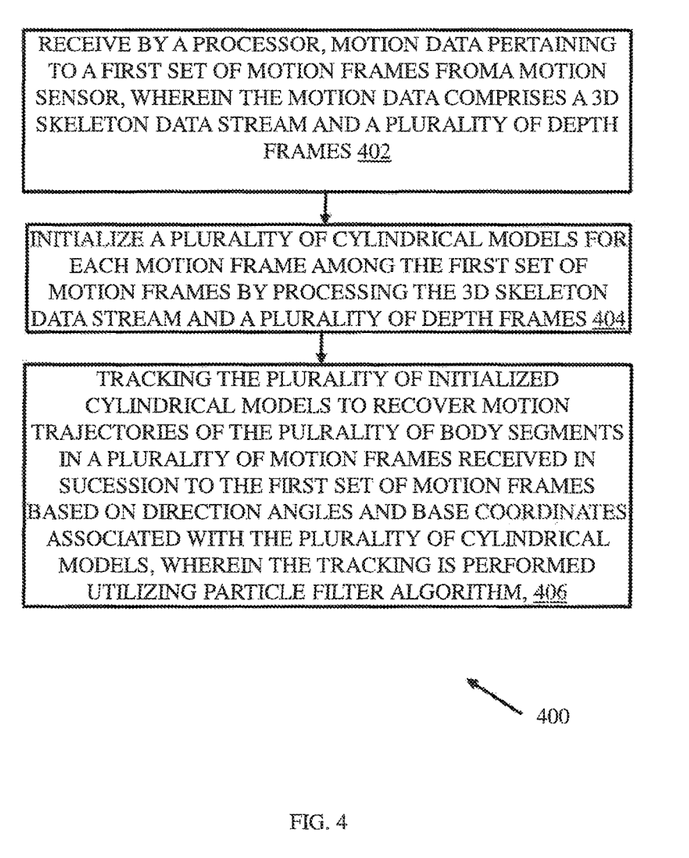
FIG. 4 illustrates a detailed flow diagram for tracking body joints, according to some embodiments of the present disclosure.

FIG. 4 illustrates a flow diagram of a method 400 for body joint tracking, according to some embodiments of the present disclosure. The method 400 may be described in the general context of computer executable instructions. Generally, computer executable instructions can include routines, programs, objects, components, data structures, procedures, modules, functions, etc., that perform particular functions or implement particular abstract data types. The method 400 may also be practiced in a distributed computing environment where functions are performed by remote processing devices that are linked through a communication network. The order in which the method 400 is described is not intended to be construed as a limitation, and any number of the described method blocks can be combined in any order to implement the method 400, or an alternative method. Furthermore, the method 400 can be implemented in any suitable hardware, software, firmware, or combination thereof.

At 402, the system 200 receives, by the one or more hardware processors, motion data pertaining to a first set of motion frames from the motion sensor device. Here, the motion data comprises the initial joint motion data and a plurality of depth frames. The initial joint motion data comprises 3 dimensional world coordinates of the plurality of body joints associated with the plurality of depth frame and each depth frame among the plurality of depth frames comprises the set of 2 dimensional image coordinates and the depth value. At 404, the system 200 initializes a plurality of cylindrical models, by the one or more hardware processors, for each motion frame among the first set of motion frames by processing the initial joint motion data and the plurality of depth frames. Here, the plurality of cylindrical models represents the plurality of body segments, connecting adjacent body joints among the plurality of body joints. Further, the plurality of 3 dimensional point clouds corresponding to the plurality of depth frames are obtained by mapping every 2 dimensional image coordinates to the 3 dimensional world coordinates. The plurality of 3 dimensional point clouds are segmented based on a segmentation threshold to obtain a first set of segmented 3 dimensional point clouds. Here, the first set of segmented 3 dimensional point clouds corresponds to the plurality of body segments. Additionally, the segmentation threshold is obtained based on a Euclidean distance computed for 3 dimensional world coordinates corresponding to the plurality of body joints of the initial joint motion data. Further, the first set of segmented 3 dimensional point clouds corresponding to the plurality of body segments are smoothened prior to model fitting to reduce one or more model outliers. Further, the plurality of cylindrical models are fitted to the set of smoothened point clouds corresponding to the plurality of body segments associated with each motion frame among the first set of motion frames. The set of cylinder coefficients of each cylindrical model among the plurality of cylindrical models includes radius, length, one or more direction angles and one or more base coefficients. The radius of the plurality of cylindrical models are initialized to a mean radius value obtained from the cylinder radius corresponding to the plurality of motion frames. The one or more direction angles of the plurality of cylindrical models are initialized to a mean direction value obtained from a cylinder directions corresponding to the plurality of motion frames. The one or more base coordinates of the plurality of cylindrical models are initialized to an average base value obtained by projecting a plurality of joint center coordinates in the initial joint motion data to an axis of a corresponding cylindrical model from the plurality of motion frames. The length of the plurality of cylindrical models are initialized to a mean length value obtained from a distance between adjacent body joints in the initial joint motion data for the plurality of motion frames. At 406, the system 200 tracks, by the one or more hardware processors, the plurality of initialized cylindrical models to obtain one or more optimized motion trajectories of the plurality of body joints in a plurality of motion frames received in succession to the first set of motion frames based on the one or more direction angles and the one or more base coordinates associated with each of the plurality of cylindrical models. Here, the tracking is performed by utilizing the particle filter mechanism, the particle filter mechanism receives the plurality of initialized cylindrical models and the second set of segmented point cloud data corresponding to the plurality of motion frames received in succession to the first set of motion frames from the motion sensor device. Here, the initialized plurality of cylindrical models are represented as a plurality of particles. Each particle among the plurality of particles comprises a state represented by the one or more direction and the one or more base coordinates and a weight. The state of the plurality of particles are propagated to a new state and the state is updated based on the state propagation rule by utilizing the state space model, wherein the state propagation rule is based on the plurality of initialized cylindrical models. The weight associated with the plurality of particles are updated based on the likelihood function and the weight update rule by utilizing an observation model, wherein the weight update rule is based on the second set of segmented point cloud data and the plurality of initialized cylindrical models. Further, the plurality of initialized cylindrical models are tacked based on the state and the weight of the plurality of particles associated with the plurality of initialized cylindrical models to obtain the optimized motion trajectories of the plurality of body joints.

Figure 5A:
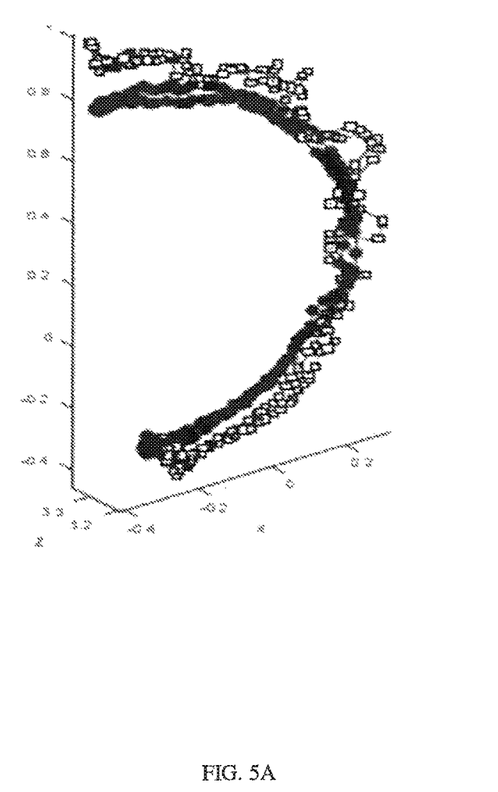
FIG. 5A illustrates an example 3 dimensional temporal trajectory of wrist joint during shoulder abduction, according to some embodiments of the present disclosure.
Figure 5B:
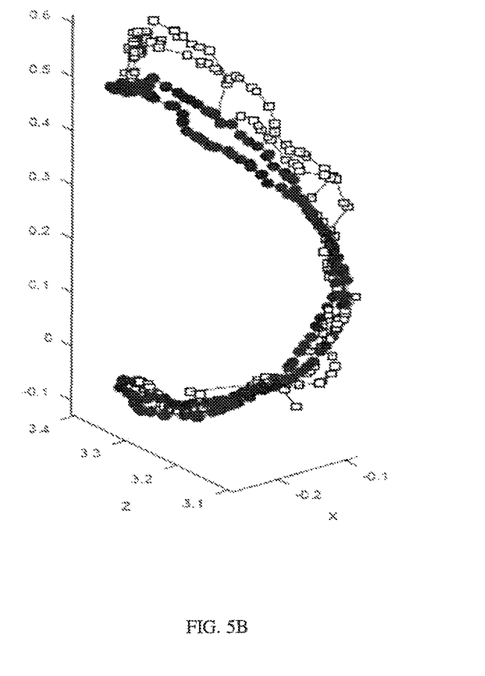
FIG. 5B illustrates an example 3 dimensional temporal trajectory of elbow joint during shoulder flexion, according to some embodiments of the present disclosure.
Figure 5C:
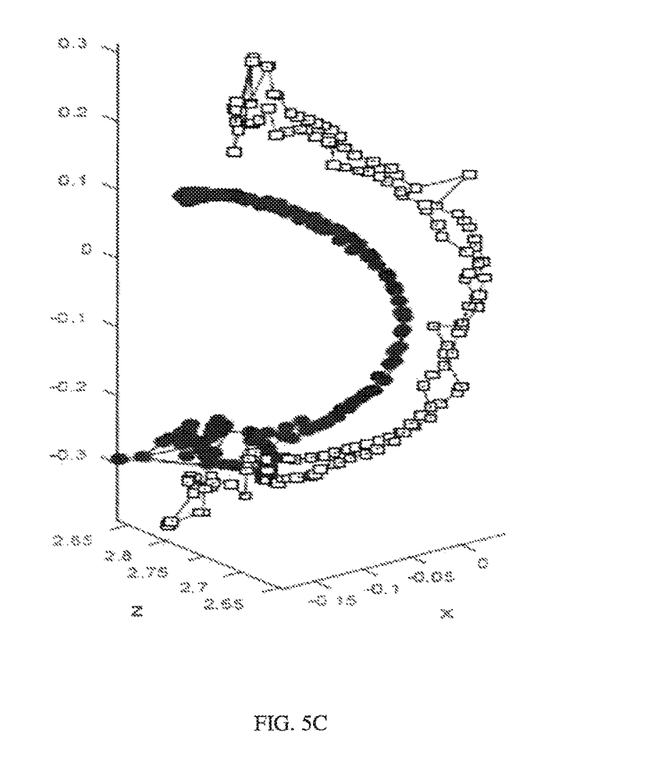
FIG. 5C illustrates an example 3 dimensional temporal trajectory of wrist joint during elbow flexion, according to some embodiments of the present disclosure.

In an embodiment, the system 200 is experimented as follows: The temporal trajectory of a joint among the plurality of joints moving with respect to a stationary pivot joint (e.g trajectory of the elbow about the shoulder joint during shoulder abduction) is analyzed for motion smoothness and variation of radius. FIG. 5A to 5C illustrates examples of 3 dimensional trajectory plots comparing smoother trajectory of motion and lesser variation in radius of the trajectories obtained after applying the present disclosure, with Kinect® V1 skeletal tracking. Particularly, FIG. 5A illustrates an example 3 dimensional temporal trajectory of wrist joint during shoulder abduction, according to some embodiments of the present disclosure. Here, a plot with black circles illustrates the temporal trajectory of the wrist obtained through the present disclosure and a plot with white squares illustrates the temporal trajectory of the wrist obtained through Kinect® V1. FIG. 5B illustrates an example 3 dimensional temporal trajectory of elbow joint during shoulder flexion, according to some embodiments of the present disclosure. Here, the plot with black circles illustrates the temporal trajectory of elbow joint during shoulder flexion obtained through the present disclosure and the plot with white squares illustrates the temporal trajectory of elbow joint during shoulder flexion obtained through Kinect® V1. FIG. 5C illustrates an example 3 dimensional temporal trajectory of wrist joint during elbow flexion, according to some embodiments of the present disclosure. Here, the plot with black circles illustrates the temporal temporal trajectory of wrist joint during elbow flexion obtained through the present disclosure and the plot with white squares illustrates the temporal temporal trajectory of wrist joint during elbow flexion obtained through Kinect® V1.

In an embodiment, the following performance metrics are computed: (i) root-mean-squared error (RMSE), (ii) coefficient of variation (CV) of the radius of curvature, and (iii) a measure for motion smoothness. The RMSE is computed with respect to a reference radius of curvature (equal to the body segment length) estimated during initialization of the plurality of cylinders. The coefficient of variation (CV) is a measure of trajectory spread that describes the ratio of variance to mean of the trajectory radius. The smoothness of a function $f(x)$ approximating the trajectory points over an interval $[a;b]$ is measured by function $g(f(x))$ referred to as equation 6, mainly used for smoothing spline interpolation. A lower value of $g(f(x))$ indicates greater smoothness of $f(x)$.

$$g(f(x)) = \int_a^b (f''(x))^2 dx \quad \rightarrow (6)$$

TABLE I

| ROM Exercise | Trajectory of joint | Method | Coefficient of variation | RMSE (in mm) | Smoothness coefficient |
| --- | --- | --- | --- | --- | --- |
| Shoulder Abduction-Adduction | Elbow | Kinect ® V1 | 0.128870 | 0.051360 | 0.063295 |
| | | Present disclosure | 0.091506 | 0.042277 | 0.043249 |
| | Wrist | Kinect ® V1 | 0.084366 | 0.130863 | 0.184191 |

TABLE I-continued

| ROM Exercise | Trajectory of joint | Method | Coefficient of variation | RMSE (in mm) | Smoothness coefficient |
|---|---|---|---|---|---|
| | | Present disclosure | 0.053918 | 0.044017 | 0.077605 |
| Shoulder Flexion-Extension | Elbow | Kinect ® V1 | 0.101716 | 0.039362 | 0.039370 |
| | | Present disclosure | 0.070454 | 0.028332 | 0.028636 |
| | Wrist | Kinect ® V1 | 0.060563 | 0.128109 | 0.092172 |
| | | Present disclosure | 0.042490 | 0.028614 | 0.043032 |
| Elbow Flexion-Extension | Wrist | Kinect ® V1 | 0.069170 | 0.086471 | 0.017815 |
| | | Present disclosure | 0.038571 | 0.023394 | 0.016184 |
| Percentage of Improvement | | | 33.98 | 52.54 | 35.85 |

Further, the average performance measures over the entire dataset are summarized in Table I. The results indicate a 34% reduction in CV, 53% reduction in RMSE, and 36% improvement in motion smoothness of temporal trajectories using the present disclosure tracking framework when compared to Kinect® V1. Hence an overall improvement in the accuracy of joint motion trajectories is obtained using the present disclosure on Kinect® V1, rendering it more suitable for clinical evaluation and rehabilitation purposes.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Various embodiments disclose methods and system for tracking body joints are able to track the trajectories of the plurality of joints associated with the plurality of body segments in an optimized manner. Here, the tracking is performed based on the direction angles and base coordinates of the plurality of initialized cylindrical models. Additionally, the optimization is performed using the state space model and the observation model. The state propagation in the state space model is determined by utilizing the state propagation rule and the weight updating is performed in the observation model by utilizing the weight updating rule.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for tracking body joints, the method comprising:
receiving, by one or more hardware processors, motion data pertaining to a first set of motion frames from a motion sensor device, wherein the motion data comprises an initial joint motion data and a plurality of depth frames, wherein the initial joint motion data comprises locations in 3 dimensional world coordinates of a plurality of body joints associated with the plurality of depth frames and each depth frame among the plurality of depth frames comprises a set of 2D image coordinates and a depth value;
initializing, by the one or more hardware processors, a plurality of cylindrical models for each motion frame among the first set of motion frames by processing the initial joint motion data and the plurality of depth frames, wherein the plurality of cylindrical models represents a plurality of body segments, connecting adjacent body joints among the plurality of body joints, and wherein initializing the plurality of cylindrical models for each motion frame among the first set of motion frames comprises:
obtaining a plurality of 3 dimensional point clouds corresponding to the plurality of depth frames by mapping every 2 dimensional image coordinates to the 3 dimensional world coordinates, based on a perspective projection;
segmenting the plurality of 3 dimensional point clouds based on a segmentation threshold to obtain a first set of segmented 3 dimensional point clouds, wherein the first set of segmented 3 dimensional point clouds corresponds to the plurality of body segments, wherein the segmentation threshold is obtained based on an Euclidean distance computed for 3 dimensional world coordinates corresponding to the plurality of body joints of the initial joint motion data;
smoothening and reconstructing the first set of segmented 3 dimensional point clouds corresponding to the plurality of body segments prior to model fitting to reduce one or more model outliers, by using a Moving Least Squares (MLS) mechanism; and
fitting the plurality of cylindrical models to the set of smoothened point clouds corresponding to the plurality of body segments associated with each motion frame among the first set of motion frames, wherein a set of cylinder coefficients of each cylindrical model among the plurality of cylindrical models includes radius, length, the one or more direction angles and the one or more base coordinates; and
tracking, by the one or more hardware processors, the plurality of initialized cylindrical models to obtain one or more an optimized motion trajectories of the plurality of body joints in a plurality of motion frames received in succession to the first set of motion frames based on one or more direction angles and one or more base coordinates associated with each of the plurality of cylindrical models, wherein the tracking is performed by utilizing a particle filter mechanism, and wherein tracking the plurality of initialized cylindrical models to obtain an optimized motion trajectories comprises:
receiving the plurality of initialized cylindrical models and a second set of segmented point cloud data corresponding to the plurality of motion frames received in succession to the first set of motion frames from the motion sensor device, wherein the initialized plurality of cylindrical models are represented as a plurality of particles, and wherein each particle among the plurality of particles comprises a state represented by the one or more direction angles and the one or more base coordinates, and a weight;
propagating the plurality of particles to a new state and updating the state based on a state propagation rule by utilizing a state space model, wherein the state propagation rule is based on the plurality of initialized cylindrical models and variance of Gaussian noise with zero mean for the one or more direction angles and the one or more base coordinates;
updating the weight associated with the plurality of particles based on a variance of Gaussian likelihood function and a weight update rule by utilizing an observation model, wherein the weight update rule is based on the second set of segmented point cloud data and the plurality of initialized cylindrical models, and wherein the weight update rule considers a distance (D), which is a sum of all distances (d) of the second set of segmented point cloud data from a cylindrical model represented by a particle for which the weight is being updated; and
tracking the plurality of initialized cylindrical models based on the state and the weight of the plurality of particles associated with the plurality of initialized cylindrical models to obtain the optimized motion trajectories of the plurality of body joints, wherein a cylindrical model among the plurality of initialized cylindrical model having maximum weight is selected as an optimal cylindrical model.

2. The processor implemented method of claim 1, wherein initializing the plurality of cylindrical models for each motion frame among the first set of motion frames further comprises:
initializing the radius of the plurality of cylindrical models, a mean radius value obtained from a cylinder radius corresponding to the plurality of motion frames;
initializing the one or more direction angles of the plurality of cylindrical models, a mean direction value obtained from a set of cylinder directions corresponding to from the plurality of motion frames;
initializing the one or more base coordinates of the plurality of cylindrical models, an average base value obtained by projecting a plurality of joint center coordinates in the initial joint motion data to an axis of a corresponding cylindrical model from the plurality of motion frames; and
initializing the length of the plurality of cylindrical models, a mean length value obtained from a distance between adjacent body joints in the initial joint motion data stream for plurality of motion frames.

3. A body joint tracking system, the system comprising:
a motion sensor device;
one or more memories comprising programmed instructions; and
one or more hardware processors operatively coupled to the one or more memories, wherein the one or more hardware processors are configured to execute the programmed instructions stored in the one or more memories to:
receive, motion data pertaining to a first set of motion frames from the motion sensor device, wherein the motion data comprises an initial joint motion data and a plurality of depth frames, wherein the initial joint motion data comprises locations in 3 dimensional world coordinates of a plurality of body joints associated with the plurality of depth frames and each depth frame among the plurality of depth frames comprises a set of 2D image coordinates and a depth value;
initialize, a plurality of cylindrical models for each motion frame among the first set of motion frames by processing the initial joint motion data and the plurality of depth frames, wherein the plurality of cylindrical models represents a plurality of body segments, connecting adjacent body joints among the plurality of body joints, and wherein initializing the plurality of cylindrical models for each motion frame among the first set of motion frames comprises:
obtaining a plurality of 3 dimensional point clouds corresponding to the plurality of depth frames by mapping every 2 dimensional image coordinates to the 3 dimensional world coordinates, based on a perspective projection;
segmenting the plurality of 3 dimensional point clouds based on a segmentation threshold to obtain a first set of segmented 3 dimensional point clouds, wherein the first set of segmented 3 dimensional point clouds corresponds to the plurality of body segments, wherein the segmentation threshold is obtained based on an Euclidean distance computed for 3 dimensional world coordinates corresponding to the plurality of body joints of the initial joint motion data;
smoothening and reconstructing the first set of segmented 3 dimensional point clouds corresponding to the plurality of body segments prior to model fitting to reduce one or more model outliers, by using a Moving Least Squares (MLS) mechanism; and
fitting the plurality of cylindrical models to the set of smoothened point clouds corresponding to the plurality of body segments associated with each motion frame among the first set of motion frames, wherein a set of cylinder coefficients of each cylindrical model among the plurality of cylindrical models includes radius, length, the one or more direction angles and the one or more base coordinates; and
track, the plurality of initialized cylindrical models to obtain one or more optimized motion trajectories of the plurality of body joints in a plurality of motion frames received in succession to the first set of motion frames based on a set of direction angles and a set of base coordinates associated with each of the plurality of cylindrical models, wherein the tracking is performed by utilizing a particle filter mechanism, and wherein tracking the plurality of initialized cylindrical models to obtain an optimized motion trajectories comprises:
receiving the plurality of initialized cylindrical models and a second set of segmented point cloud data corresponding to the plurality of motion frames received in succession to the first set of motion frames from the motion sensor device, wherein the initialized plurality of cylindrical models are represented as a plurality of particles, and wherein each particle among the plurality of particles comprises a state represented by the one or more direction angles and the one or more base coordinates, and a weight;
propagating the plurality of particles to a new state and updating the state based on a state propagation rule by utilizing a state space model, wherein the state propagation rule is based on the plurality of initialized cylindrical models and variance of Gaussian noise with zero mean for the one or more direction angles and the one or more base coordinates;
updating the weight associated with the plurality of particles based on a variance of Gaussian likelihood function and a weight update rule by utilizing an observation model, wherein the weight update rule is based on the second set of segmented point cloud data and the plurality of initialized cylindrical models, and wherein the weight update rule considers a distance (D), which is a sum of all distances (d) of the second set of segmented point cloud data from a cylindrical model represented by a particle for which the weight is being updated; and
tracking the plurality of initialized cylindrical models based on the state and the weight of the plurality of particles associated with the plurality of initialized cylindrical models to obtain the optimized motion trajectories of the plurality of body joints, wherein a cylindrical model among the plurality of initialized cylindrical model having maximum weight is selected as an optimal cylindrical model.

4. The system of claim 3, wherein the one or more hardware processors are further configured to initialize the plurality of cylindrical models for each motion frame among the first set of motion frames by:
initializing the radius of the plurality of cylindrical models, a mean radius value obtained from a cylinder radius corresponding to the plurality of motion frames;
initializing the one or more direction angles of the plurality of cylindrical models, a mean direction value obtained from a set of cylinder directions corresponding to from the plurality of motion frames;
initializing the one or more base coordinates of the plurality of cylindrical models, an average base value obtained by projecting a plurality of joint center coordinates in the initial joint motion data to an axis of a corresponding cylindrical model from the plurality of motion frames; and
initializing the length of the plurality of cylindrical models, a mean length value obtained from a distance between adjacent body joints in the initial joint motion data stream for plurality of motion frames.

5. One or more non-transitory machine readable information storage mediums comprising one or more instructions which when executed by one or more hardware processors causes:
receiving, by the one or more hardware processors, motion data pertaining to a first set of motion frames from a motion sensor device, wherein the motion data comprises an initial joint motion data and a plurality of depth frames, wherein the initial joint motion data comprises locations in 3 dimensional world coordinates of a plurality of body joints associated with the plurality of depth frames and each depth frame among the plurality of depth frames comprises a set of 2D image coordinates and a depth value;

initializing, by the one or more hardware processors, a plurality of cylindrical models for each motion frame among the first set of motion frames by processing the initial joint motion data and the plurality of depth frames, wherein the plurality of cylindrical models represents a plurality of body segments, connecting adjacent body joints among the plurality of body joints, and wherein initializing the plurality of cylindrical models for each motion frame among the first set of motion frames comprises:

obtaining a plurality of 3 dimensional point clouds corresponding to the plurality of depth frames by mapping every 2 dimensional image coordinates to the 3 dimensional world coordinates, based on a perspective projection;

segmenting the plurality of 3 dimensional point clouds based on a segmentation threshold to obtain a first set of segmented 3 dimensional point clouds, wherein the first set of segmented 3 dimensional point clouds corresponds to the plurality of body segments, wherein the segmentation threshold is obtained based on an Euclidean distance computed for 3 dimensional world coordinates corresponding to the plurality of body joints of the initial joint motion data;

smoothening and reconstructing the first set of segmented 3 dimensional point clouds corresponding to the plurality of body segments prior to model fitting to reduce one or more model outliers, by using a Moving Least Squares (MLS) mechanism; and  fitting the plurality of cylindrical models to the set of smoothened point clouds corresponding to the plurality of body segments associated with each motion frame among the first set of motion frames, wherein a set of cylinder coefficients of each cylindrical model among the plurality of cylindrical models includes radius, length, the one or more direction angles and the one or more base coordinates; and tracking, by the one or more hardware processors, the plurality of initialized cylindrical models to obtain one or more an optimized motion trajectories of the plurality of body joints in a plurality of motion frames received in succession to the first set of motion frames based on one or more direction angles and one or more base coordinates associated with each of the plurality of cylindrical models, wherein the tracking is performed by utilizing a particle filter mechanism, and wherein tracking the plurality of initialized cylindrical models to obtain an optimized motion trajectories comprises:

receiving the plurality of initialized cylindrical models and a second set of segmented point cloud data corresponding to the plurality of motion frames received in succession to the first set of motion frames from the motion sensor device, wherein the initialized plurality of cylindrical models are represented as a plurality of particles, and wherein each particle among the plurality of particles comprises a state represented by the one or more direction angles and the one or more base coordinates, and a weight;

propagating the plurality of particles to a new state and updating the state based on a state propagation rule by utilizing a state space model, wherein the state propagation rule is based on the plurality of initialized cylindrical models and variance of Gaussian noise with zero mean for the one or more direction angles and the one or more base coordinates;

updating the weight associated with the plurality of particles based on a variance of Gaussian likelihood function and a weight update rule by utilizing an observation model, wherein the weight update rule is based on the second set of segmented point cloud data and the plurality of initialized cylindrical models, and wherein the weight update rule considers a distance (D), which is a sum of all distances (d) of the second set of segmented point cloud data from a cylindrical model represented by a particle for which the weight is being updated; and  tracking the plurality of initialized cylindrical models based on the state and the weight of the plurality of particles associated with the plurality of initialized cylindrical models to obtain the optimized motion trajectories of the plurality of body joints, wherein a cylindrical model among the plurality of initialized cylindrical model having maximum weight is selected as an optimal cylindrical model.

\* \* \* \* \*